United States Patent [19]

Tietjen et al.

[11] Patent Number: 4,574,082

[45] Date of Patent: Mar. 4, 1986

[54] ONE-PHASE SILICONE-BASED COSMETIC PRODUCTS CONTAINING WAX

[75] Inventors: Marlene Tietjen; Jane Hollenberg, both of New York; Richard T. Rigg, Brooklyn, all of N.Y.

[73] Assignee: Revlon, Inc., New York, N.Y.

[21] Appl. No.: 518,497

[22] Filed: Jul. 29, 1983

[51] Int. Cl.⁴ .................... A61K 7/021; A61K 7/025
[52] U.S. Cl. ........................................ 424/63; 424/64; 424/DIG. 5; 514/772
[58] Field of Search ............... 424/63, 64, 69, 70, 424/357, DIG. 5; 514/772

[56] References Cited

U.S. PATENT DOCUMENTS

| | | | |
|---|---|---|---|
| 3,641,239 | 2/1972 | Mohrlok | 424/64 |
| 4,126,679 | 11/1978 | Davy et al. | 424/66 |
| 4,355,046 | 10/1982 | Siiess | 514/772 |
| 4,390,524 | 6/1983 | Nasuno et al. | 424/63 |
| 4,423,032 | 12/1983 | Abe et al. | 424/70 |
| 4,423,041 | 12/1983 | Clum et al. | 424/68 X |

OTHER PUBLICATIONS

Dow Corning Corp., product bulletin for "Dow Corning 200" Fluid.
CTFA Cosmetic Ingredient Dictionary, pp. 83 and 402.
Chem. Abs. 96:40742g, (1982).

Primary Examiner—Robert J. Warden
Assistant Examiner—Shawn P. Foley

[57] ABSTRACT

Cosmetic products which do not suffer phase separation comprise a mixture of a cosmetically acceptable wax with dimethylpolysiloxane and either an organosilane or an organically substituted polysiloxane.

19 Claims, No Drawings

ONE-PHASE SILICONE-BASED COSMETIC PRODUCTS CONTAINING WAX

BACKGROUND OF THE INVENTION

This invention relates to cosmetic products in stick, cake, or cream form such as eyeshadows, foundations, moisturizers, and skin protectants. More specifically, the invention relates to such cosmetic products which contain a silicone base, e.g. dimethylpolysiloxane fluid. This fluid has the chemical formula

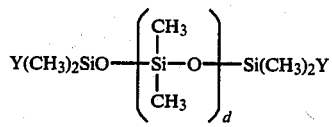  (1)

wherein both Y substituents are —$CH_3$, or both are —OH, and in which the degree of polymerization d is a value, typically between 1 and 150, effective to give the fluid a viscosity of 0.65 to 1 million centistokes at 25° C. (Viscosity of such fluids can be measured by widely recognized test methods, such as the spinning cup test.)

Although dimethylpolysiloxane fluids offer the properties of water repellency, slip, non-greasy emollience, and low penetration of the skin, their use in anhydrous cream and stick products is limited by their poor physical compatibility when combined with other common cosmetic ingredients such as waxes. In particular, the dimethylpolysiloxane fluids are immiscible with waxes; a molten mixture of such a fluid and a wax can be maintained homogeneous only with determined stirring, and cooling such a molten mixture forms a product which undergoes phase separation and forms a mushy or pasty solid which is mixed with a nearly liquid fluid phase. In addition, many conventional pigments are very difficult to mix in silicone fluids such as dimethylpolysiloxane.

It is therefore highly desirable to provide a stick or cream cosmetic product which includes one or more waxes and dimethylpolysiloxane and which is a homogeneous, single-phase product, yet provides the non-greasy feel, excellent slip, and adhesion of the dimethylpolysiloxane fluid when applied to the skin.

SUMMARY OF THE INVENTION

An anhydrous cosmetic composition comprising
(a) 2 to 50 wt. % of dimethylpolysiloxane having the formula

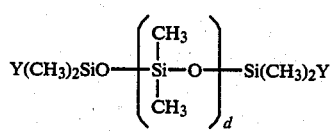

wherein the Y substituents are both —$CH_3$ or both —OH, and wherein the degree of polymerization d is sufficient to provide the dimethylpolysiloxane with a viscosity of 0.65 to $10^6$ centistokes at 25° C.;

(b) 2 to 50 wt. % of an organosilane having the formula $RSi(CH_3)_3$ or an organo-polysiloxane having the formula

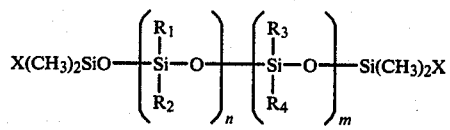

or mixtures thereof, wherein R is alkyl having 1 to 30 carbon atoms, or aryl;

$R_1$ and $R_3$ are independently alkyl having 1 to 30 carbon atoms, or aryl;

X is alkyl or alkoxy and has 1 to 30 carbon atoms;

$R_2$ is alkyl having 2 to 30 carbon atoms, aryl, or trimethylsiloxy (($CH_3$)$_3$SiO—);

$R_4$ is alkyl having 2 to 30 carbon atoms, or aryl;

n is 1 to 100, m is 0 to 100, and (n plus m) is 1 to 100; and (c) 4 to 20 wt. % of a cosmetically acceptable wax; provided that there is a sufficient amount of component (b) present that the product formed by cooling to 25° C. a molten, stirred mixture of components (a), (b) and (c) is a single homogeneous phase.

DETAILED DESCRIPTION OF THE INVENTION

Cosmetic compositions in accordance with this invention include 2 to 50 wt. %, preferably 10 to 40 wt. %, and more preferably 20 to 40 wt. %, of dimethylpolysiloxane having the formula (1) given above and a viscosity (at 25° C.) of about 0.65 to about 1,000,000 centistokes (abbreviated herein as "cs"). Preferred fluids have a viscosity of about 5 to about 500 centistokes.

The compositions also contain 2 to 50 wt. %, preferably 5 to 40 wt. %, and more preferably 5 to 25 wt. %, of an organosilane having the formula $RSi(CH_3)_3$ or an organo-polysiloxane having

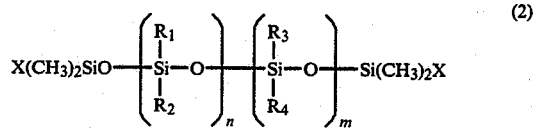  (2)

wherein n is 1 to 100, m is 0 to 100, and the sum (n+m) is 1 to 100. In the above formulas, R is alkyl having 1 to 30 carbon atoms, or aryl; $R_1$ and $R_3$ are independently alkyl having 1 to 30 carbon atoms or aryl; $R_2$ is alkyl having 2 to 30 carbon atoms, aryl or trimethylsiloxy; and $R_4$ is alkyl having 2 to 30 carbon atoms, or aryl. As used herein, "alkyl" and the alkyl moiety of "alkoxy" includes straight- and branched-chain aliphatic groups having 1 to 30 carbon atoms; examples include methyl, ethyl, octyl, and octadecyl. Preferred aryl groups include phenyl and groups in which a phenyl ring is connected to the Si by an alkyl or alkylene bridge up to 3 carbons long, such as styryl. Preferably at least one of $R_1$, $R_2$, $R_3$ and $R_4$ is alkyl. X is alkyl, or alkyl-oxy, wherein the alkyl group has 1 to 30 carbon atoms; examples of such groups are methyl and octadecyl. Examples of the R group in the formula $RSi(CH_3)_3$ include octadecyl and stearoxy.

Examples of organo-polysiloxanes where m equals zero are polymethyloctyl-siloxane, polymethyloctadecyl-siloxane, polymethylphenyl-siloxane, and octadecyloxydimethylpolydimethyl-siloxane. Examples where n and m are both non-zero include polymethyl/- polymethylphenyl-siloxane, polymethylstyryl/polymethylethyl-siloxane, and polymethylstyryl/polymethyldodecyl-siloxane. In this nomenclature, the one or two substituents named after the "poly" are each attached to the silicon atom in each repeating unit, and substituents before "poly" are attached to both ends of the polymer chain. To illustrate, "polymethyloctylsiloxane" means a compound of formula (2) in which m is zero, $R_1$ is methyl, and $R_2$ is octyl. Furthermore, the term "polymethylstyryl/polymethyl-dodecyl-siloxane" means a compound of formula (2) wherein $R_1$ is methyl, $R_2$ is styryl (e.g. $C_6H_5CH:CH-$), $R_3$ is methyl, and $R_4$ is dodecyl (e.g. $C_{12}H_{25}-$).

The cosmetic composition also contains 4 to 20 wt. % and preferably 6 to 15 wt. % of a cosmetically acceptable wax; those of ordinary skill in this art will readily identify what is meant by this term. Examples are carnauba, ozokerite, glyceryl tribehenate, beeswax, candelilla, paraffin, bayberry wax, lanolin, microcrystalline wax, montan, rice wax, solid mono-, di- or triglycerol esters of $C_{12}-C_{36}$ fatty acids, polyethylene, polyethylene/polyvinylacetate copolymers, polyethylene/polyacrylic acid copolymers, $C_{12}-C_{36}$ fatty alcohols, and solid esters of $C_{12}-C_{36}$ fatty alcohols and acids, provided that the wax used in this invention is solid at room temperature (25° C.) The useful waxes are further characterized in that they have crystalline to microcrystalline structure; leave a film when applied to the skin from a cosmetic stick or cream; have low viscosity just above their melting points; and exhibit low solubility at room temperature in the dimethylpolysiloxane described hereinabove. Typically the waxes are high-molecular-weight hydrocarbons ($C_{12}-C_{100}$) or mixtures thereof, esters of high-molecular-weight fatty acids with high-molecular-weight fatty alcohols, or mono-, di-, or triesters of $C_{12}-C_{36}$ fatty acids with glycerol.

The cosmetic composition should contain enough of the organo-polysiloxane of formula (2) described above to provide that the composition, whether it is a stick, a cake, or a cream, is a single homogeneous phase. That is, at a temperature above the melting point of the highest-melting ingredient, one should be able to stir together a molten mixture of the three components (dimethylpolysiloxane, organo-polysiloxane, and wax) easily using conventional mixing equipment; and then, on discontinuing stirring, the components should not separate into discrete layers or areas of different composition. Likewise, when a stirred, molten mixture of the three components is cooled to 25° C., the cooled product should remain one continuous phase and the wax should not ooze, bleed, or otherwise separate from the silane and/or siloxane components. In general, the proper relative amounts of wax and the two silicone components can readily be determined by examination of the behavior of a sample formulation; as a general guide to formulations known to be successful, the weight percentage of the wax can be up to about one-third of the combined weight percentage of the silicone components, and the weight ratio of organo-polysiloxane or organosilane to dimethylpolysiloxane can be up to about 1:1. Variations from these figures are also contemplated within the broad aspect of the present invention, however, so long as the proportions chosen permit the creation of a physically stable one-phase cosmetic product.

To make the cosmetic composition of the invention, one stirs the dimethylpolysiloxane component with any other liquid components (such as the organo-polysiloxane, if it is liquid at room temperature) to achieve a uniform mixture. Any of the optional components which are initially dry (such as fillers, preservatives, and pigments, including the novel pigments described below) are then added to the liquid mixture and dispersed using high shear equipment (such as a 3-roll mixer or Kady mill) until a homogeneous dispersion is obtained. This dispersion is then heated to a point above the melting temperature of the wax material which is to be added (usually 60°-95° C.). The wax, and the organopolysiloxane if it is solid at room temperature, are added and stirred with a high-shear mixer until all components are melted and dispersed uniformly. The melted mixture is poured hot (at 60°-95° C.) into the containers of choice, e.g. pans, jars, or sticks, where it is permitted to cool to room temperature.

The resulting product can be used per se as a cosmetic which is applied to soothe and moisturize the skin. One can also add optional ingredients such as cosmetically acceptable fillers, pigments, and/or fragrance. These ingredients are added in finely divided form to the molten mixture, with stirring, before the mixture is poured into containers. As is well recognized in this field, many materials can serve simultaneously as fillers, to add body to the product, and as colorants, to make the product white or a shade such as red. Examples of fillers are talc, mica, silica, kaolin, magnesium silicate, magnesium carbonate, calcium silicate, calcium carbonate, powdered nylon, and combinations thereof. Examples of colorants include iron oxide, titanium dioxide, talc, mica, ultramarine, bismuth oxychloride, chromium oxides, chromium hydroxide, carmine, manganese violet, ferric ferrocyanide, FDA certified organic dyes and lakes, metallic powders, and equivalents. The total of fillers plus colorants can comprise up to 60 wt. % of the product of this invention. The cosmetic formulator will recognize that a blend of fragrance oils such as is conventionally supplied by fragrance manufacturers can be added, in amounts generally ranging up to about 0.5 wt. %. As preservatives one can use methyl or propyl paraben or their equivalent, in amounts up to about 0.5 wt. %.

The composition can contain up to about 40 wt. % and preferably up to about 20 wt. % of one or more cosmetically acceptable oils, to further augment the feel of the product on the skin and to adjust the product's consistency. Suitable oils include glycerol esters and $C_3-C_{22}$ alcohol esters of $C_3-C_{22}$ fatty acids, and $C_{12}-C_{22}$ fatty alcohols, provided that they are liquid at 25° C. The ordinarily skilled formulator will recognize that other compounds known to be equivalent to those listed herein can be incorporated into the composition of this invention.

The invention is further described in the following Examples.

In each Example, all components that are liquid at 25° C. were mixed together at room temperature, and then the dry ingredients (preservatives, fillers, pigments) were mixed into the liquid using high-shear equipment. When the resulting mixture was homogeneous and all solid components were uniformly dispersed, the mixture was heated to above the melting point of the wax that was about to be added (or above the highest melting point if more than one wax was added), and then the wax was added and stirred into the mixture. If the organopolysiloxane or organosilane is a solid at 25° C., it was added at the same time as the wax. The entire mixture was stirred using conventional equipment (Lightnin brand mixer or Kady brand mill) until a uniform mixture was obtained. The mixture was poured hot (60°-95° C.) into its intended package. No phase separation or component segregation occurred during or after cooling of the product. All solid ingredients which were added as finely divided powders had a particle size typically less than 50 microns. Materials whose crystalline structure promotes the formation of flakes rather than powders (such as mica) were typically less than 150 microns in the longer dimension.

This procedure was used for the following products, which had the indicated components. All amounts are in percent by weight of the final product. Formulations in which each of the amounts indicated below differs by up to 5 wt. % of the product above or below the indicated value are within the scope of this invention.

|  | A | B |
|---|---|---|
| Foundations A and B | | |
| Ozokerite (wax) | — | 2.0 |
| Glyceryl tribehenate (wax) | 6.0 | 6.0 |
| Polymethyloctadecyl siloxane | 6.0 | 6.0 |
| 2-ethyl-1-hexyl palmitate (oil) | 13.0 | 15.0 |
| Dimethylpolysiloxane (10 cs) | 25.0 | 24.0 |
| Titanium dioxide (pigment) | 20.0 | 18.0 |
| Iron oxide (pigment) | 10.0 | 10.0 |
| Talc (filler) | 20.0 | 19.0 |
| Foundation C | | |
| Stearyl alcohol (wax) | 12.5 | |
| Stearyl trimethyl silane | 12.5 | |
| Dimethylpolysiloxane (10 cs) | 30.0 | |
| Octyldodecanol | 2.5 | |
| Titanium dioxide (pigment) | 28.0 | |
| Iron oxides (pigment) | 5.8 | |
| Talc (filler) | 7.8 | |
| Preservatives | 0.4 | |
| Fragrance | 0.5 | |
| Eyeshadow A and B | | |
| Candelilla (wax) | 5.0 | 7.0 |
| Polymethylphenylsiloxane | 25.0 | 20.0 |
| Dimethylpolysiloxane | 25.0 | 25.0 |
| Bismuth oxychloride (pigment) | 10.0 | 7.0 |
| Mica (filler) | 10.0 | — |
| TiO₂-coated mica (pigment) | 15.0 | 15.0 |
| Ultramarine blue (pigment) | 5.0 | 10.0 |
| Iron oxide (pigment) | — | 3.0 |
| Talc (filler) | — | 13.0 |
| Chromium hydroxide | 5.0 | — |
| Blush | | |
| Glyceryl tribehenate | 7.0 | |
| Polymethyloctadecylsiloxane | 6.0 | |
| 2-ethyl-1-hexyl palmitate | 15.0 | |
| Dimethylpolysiloxane (10 cs) | 25.0 | |
| Bismuth oxychloride | 7.0 | |
| Iron oxide | 5.0 | |
| D & C Red #7 Ca lake (dye) | 2.0 | |
| Talc | 18.0 | |
| Mica | 15.0 | |
| Lip Balms A and B | | |
| Microcrystalline wax | — | 3.5 |
| Glyceryl tribehenate | 6.0 | 12.5 |
| Polymethyloctadecylsiloxane | 6.0 | 12.5 |
| Dimethylpolysiloxane (500 cs) | 25.0 | 36.0 |
| 2-ethyl-1-hexyl palmitate | 19.0 | 35.5 |
| Talc | 24.0 | — |
| Mica | 20.0 | — |

All the above products exhibited superior texture and smooth feel on the skin, and could be easily applied.

What is claimed is:

1. An anhydrous homogeneous single-phase cosmetic stick, cake or cream composition comprising:

(a) 2 to 50 wt. % of dimethylpolysiloxane having the formula

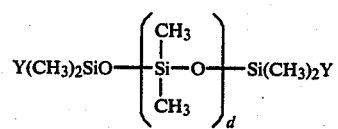

wherein the Y substituents are both —CH₃ or both —OH, and wherein the degree of polymerization d is sufficient to impart to the dimethylpolysiloxane a viscosity of 0.65 to $10^6$ centistokes at 25° C.;

(b) 2 to 50 wt. % of an organosilane having the formula RSi(CH₃)₃ or an oragano-polysiloxane having the formula

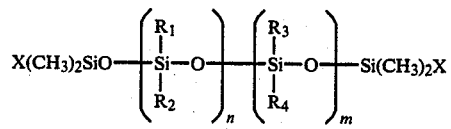

or mixtures thereof, wherein R is alkyl having 1 to 30 carbon atoms, or an aryl substituent which is phenyl or a phenyl ring connected to the Si by an alkylene bridge up to 3 carbons long or by a vinyl group;

$R_1$ and $R_3$ are independently alkyl having 1 to 30 carbon atoms, or an aryl substituent which is phenyl or a phenyl ring connected to the Si by an alkylene bridge up to 3 carbons long or by a vinyl group;

$R_2$ is alkyl having 2 to 30 carbon atoms, an aryl substituent which is phenyl or a phenyl ring connected to the Si by an alkylene bridge up to 3 carbons long or by a vinyl group, or trimethylsiloxy;

$R_4$ is alkyl having 2 to 30 carbon atoms, or an aryl substituent which is phenyl or a phenyl ring connected to the Si by an alkylene bridge up to 3 carbons long or by a vinyl group;

n is 1 to 100; m is 0 to 100; and (n plus m) is 1 to 100;

X is alkyl or alkyloxy wherein the alkyl group contains 1 to 30 carbon atoms; and (c) 4 to 30 wt. % of a cosmetically acceptable wax which does not form a homogeneous single-phase mixture with component (a); provided that there is a sufficient amount of component (b) present that the product formed by cooling to 25° C. a molten, stirred mixture of components (a), (b) and (c) is a single homogeneous phase.

2. The composition of claim 1 wherein at least one of $R_1$, $R_2$, $R_3$ and $R_4$ is alkyl provided that if $R_1$ or $R_3$ is alkyl it has 1 to 30 carbon atoms, and provided further that if $R_2$ or $R_4$ is alkyl it has 2 to 30 carbon atoms.

3. The composition of claim 1 wherein the aryl substituent is phenyl or styryl.

4. The composition of claim 1 comprising 10 to 40 wt. % of component (a), 5 to 40 wt. % of component (b), and 5 to 15 wt. % of component (c).

5. The composition of claim 1 wherein the wax is solid at 25° C. and is selected from the group consisting of carnauba, ozokerite, glyceryl tribehenate, beeswax, candelilla, paraffin, bayberry wax, lanolin, microcrystalline wax, montan, rice wax, mono-, di- and triglycerol esters of $C_{12}$-$C_{36}$ fatty acids, polyethylene, polyethylene/polyvinyl acetate copolymers, polyethylene/polyacrylic acid copolymers, $C_{12}$-$C_{36}$ fatty alcohols, and esters of $C_{12}$–$C_{36}$ fatty acids with $C_{12}$–$C_{36}$ fatty alcohols.

6. The composition of claim 1 wherein the viscosity of component (a) is 5 to 500 centistokes.

7. The composition of claim 1 wherein the alkyl groups can each contain up to 20 carbon atoms.

8. The composition of claim 1 which also contains up to about 60 wt. % of filler, colorant, or a mixture thereof.

9. The composition of claim 5 which also contains up to about 60 wt. % of filler, colorant, or a mixture thereof.

10. A composition according to claim 1 comprising 20 to 40 wt. % of component (a), 5 to 25 wt. % of component (b), and 5 to 15 wt. % of component (c).

11. A composition according to claim 10 containing by weight about 16% wax, about 12.5% polymethyloctadecyl siloxane, about 36% dimethylpolysiloxane, and about 35.5% of a cosmetically acceptable oil.

12. A composition according to claim 10 containing 40 to 50 wt. % of filler, pigment, or a mixture thereof.

13. A composition according to claim 10 containing by weight about 6% wax, about 6% polymethyloctadecyl siloxane, about 13% cosmetically acceptable oil, about 25% dimethylpolysiloxane, and about 50% pigment and filler.

14. A composition according to claim 10 containing by weight about 8% wax, about 6% polymethyloctadecyl siloxane, about 15% of a cosmetically acceptable oil, about 24% dimethylpolysiloxane, and about 47% pigment and filler.

15. A composition according to claim 10 containing by weight about 12.5% wax, about 12.5% stearyl trimethyl silane, about 30% dimethylpolysiloxane, about 42.5% pigment and filler, and the balance preservative, fragrance, and oil.

16. A composition according to claim 10 containing by weight about 5% wax, about 25% polymethylphenylsiloxane, about 25% dimethylpolysiloxane, and about 45% pigment and filler.

17. A composition according to claim 10 containing by weight about 7% wax, about 20% polymethylphenylsiloxane, about 25% dimethylpolysiloxane, and about 48% pigment and filler.

18. A composition according to claim 10 containing by weight about 7% wax, about 6% polymethyloctadecyl siloxane, about 15% cosmetically acceptable oil, about 25% dimethylpolysiloxane, and about 47% pigment and filler.

19. A composition according to claim 10 containing by weight about 6% wax, about 6% polymethyloctadecyl siloxane, about 25% dimethylpolysiloxane, about 19% cosmetically acceptable oil, and about 44% pigment and filler.

* * * * *